United States Patent [19]

Satzger

[11] Patent Number: 5,051,557
[45] Date of Patent: Sep. 24, 1991

[54] MICROWAVE INDUCED PLASMA TORCH WITH TANTALUM INJECTOR PROBE

[75] Inventor: R. Duane Satzger, West Chester, Ohio

[73] Assignee: The United States of America as represented by the Secretary of the Department of Health and Human Services, Washington, D.C.

[21] Appl. No.: 362,357

[22] Filed: Jun. 7, 1989

[51] Int. Cl.$^5$ .................................................. B23K 9/00
[52] U.S. Cl. ........................... 219/121.52; 219/121.48; 219/121.51; 315/111.21
[58] Field of Search ...................... 219/121.52, 121.51, 219/121.48, 121.36, 121.44, 10.55 R; 315/111.21, 111.51; 209/298.38, 298.37

[56] References Cited

U.S. PATENT DOCUMENTS

| | | | |
|---|---|---|---|
| 3,296,410 | 1/1967 | Hedger | 315/111.51 |
| 3,432,296 | 3/1969 | McKinnon et al. | 219/121.52 |
| 4,061,991 | 12/1977 | Hamid et al. | 315/111.21 |
| 4,423,303 | 12/1983 | Hirose et al. | 315/111.21 |
| 4,609,808 | 9/1986 | Bloyet et al. | 219/121.52 |
| 4,757,237 | 7/1988 | Hellblom et al. | 315/111.21 |
| 4,833,294 | 5/1989 | Montase et al. | 315/111.51 |
| 4,902,099 | 2/1990 | Okamoto et al. | 315/111.21 |
| 4,933,650 | 6/1990 | Okamoto | 315/111.41 |

Primary Examiner—M. H. Paschall
Attorney, Agent, or Firm—Cushman, Darby & Cushman

[57] ABSTRACT

A stable, low gas-flow microwave induce plasma torch for use with a helium microwave induced plasma system provides a toroidal plasma with central analyte injection obtained by the addition of a tantalum coupling probe injector. This, injector which penetrates through 100% of the total cavity depth, aids in plasma initiation, in the efficiency of power transfer to the cavity, and in eliminating the effects of a lack of homogeneity in the microwave field on analyte distribution in the plasma. In the preferred embodiment the microwave induced plasma torch includes a stainless steel body, a threaded aluminum insert, a PTFE insulator, a tantalum injector probe, and a quartz containment tube.

12 Claims, 6 Drawing Sheets

5,051,557

MICROWAVE INDUCED PLASMA TORCH WITH TANTALUM INJECTOR PROBE

BACKGROUND OF THE INVENTION

The present invention relates to a microwave induced plasma (MIP) torches for use an ion source for mass spectometry.

Information on trace elements is important from both nutritional and toxicological standpoints. The naturally occurring levels of trace elements in our environment are continually disturbed by today's lifestyle. The products we manufacture and consume and the fuels we use make a contribution toward shifting these natural levels. One of the roles of analytical laboratories is to develop and apply methods to determine the nature and quantity of trace elements in the environment and in our food supply.

The analyst has a wide variety of instrumental techniques (e.g., electrochemical, nuclear, spectroscopic) available which are capable of performing elemental analysis at trace levels. However, all have specific limitations such as the number of elements to which the technique is applicable, the type of sample matrix which can be handled by a particular technique, the detection limits which can be achieved, the amount of sample required for the analysis, and the time required to perform the analysis. Each of these factors plays a role in determining which technique is most appropriate for the analysis at hand.

During the past decade, the field of atomic spectrometry, which includes the most widely used techniques for elemental analysis, has undergone a shift in emphasis from the use of flames as excitation sources to the use of plasmas sustained by electromagnetic fields. The most popular analytical plasma is the radio frequency inductively coupled plasma (ICP). This plasma is widely used for generating excited state atoms and ions from samples introduced to the plasma in optical emission work and has recently generated tremendous interest as an ion source for mass spectrometry Gray, 1975; Houk, et al., 1980.

Interest in this powerful new analytical technique has steadily increased since the first report of ion sampling directly from atmospheric pressure plasma into a mass spectrometer. Prior to the development of plasma source mass spectrometry, no single instrumental technique had been potentially capable of providing sub part-per-billion detection limits for the entire periodic table at nearly simultaneous detection speeds. Using plasma mass spectrometry, elemental isotopes are separated on the basis of mass to charge ratio. Samples are introduced into the plasma source as gases or liquids without physically placing the sample inside the vacuum chamber, which is typical of conventional mass spectrometric ion sources. A schematic of an atmospheric pressure plasma sampling mass spectrometer which was built in these laboratories is shown on FIG. 6 and illustrates a sampler (a), a skimmer (b), a first vacuum stage and pumping ports (c), ion optics (d), viewing port (e), second vacuum stage diffusion pump (f), quadrupole mass analyzer (g), thrid vacuum stage turbomolecular pump (h), analog amplifier (i), and pulse amplifier (j).

Initial plasma source studies used a dc capillary arc plasma which had major drawbacks due to a low plasma gas temperature, resulting in a total ion population which contained a large percentage of low ionization potential molecular oxides Gary, 1975. The analyte response depended on the ionization potential of the element with respect to the ionization potential of the molecular oxide. As the analyte ionization potential approached that NO (ca. 9.25 eV), which was the principle ion in the mass spectrum, analyte response degraded. The NO+ originated from air entrained in the plasma. The analyte response was also suppressed by easily ionized species such as sodium which originated from the sample. This was partially due to an inability to confine the sample to the "hot" region of the plasma. These problems rendered the CAP-MS impractical for "real" sample analyses where analyte generally exists in a complex matrix. Plasmas currently under investigation as ion sources are those whose principle applications have been in optical emission work, specifically the rf inductively coupled plasma mentioned above and the microwave induced plasma.

The inductively coupled plasma (ICP) has an analyte rich central channel produced by the introduction of aqueous aerosol. This central channel has a high analyte ion density (as demonstrated by optical emission techniques) and a high gas temperature associated with this channel provides the ICP with relative freedom from matrix interferences such as ionization suppression. The relatively simple background spectrum associated with ICP-MS is produced by the ionization of the plasma gas and its impurities along with polyatomic ions produced by plasma gas atoms combining with plasma gas, oxygen, or matrix elements Tan and Horlick, 1986. Examples of atomic argon and argon containing molecular ions which interfere in elemental determinations are listed in Table 1. Major interferences are at m/z=39, 40, 41, 54, 56, 80. Materials used in the construction of the interface are also evident in the background spectra. Background intensities observed are also dependent on instrumental parameters such as plasma sampling depth, nebulizer gas flow, solution introduction rate, Rf power, and electrostatics ion lens potentials. Experiments have demonstrated that analyte signal is influenced (i.e., suppression or enhancement of analyte signal) by sample matrices which contain high levels (above 0.1%) of other ionizable elements. These matrix effects are a consideration in "real" sample analysis Satzger, 1988. The limitations and capabilities of ICP-MS in dealing with sample matrices are currently being investigated. Although matrix effects associated with ICP-MS are more pronounced than with ICP-AES, the excellent sensitivity for most elements, the multi-element capabilities, and the large linear dynamic ranges have made ICP-MS a promising technique for ultra trace elemental and isotopic analyses.

Microwave induced plasma (MIP) have been employed as atom or ion reservoirs in various analytical applications including optical emission and mass spectrometry Douglas and French, 1981; Satzger, et al., 1987; Satzger, et al., 1988. The MIP has received its only commercial acceptance as an atom specific detector for gas chromatography. In this application, analyte is separated from solvent and matrix components of the sample prior to introduction into the plasma. Therefore, the MIP, which is thermally cooler than the inductively coupled plasma, can more easily accomplish the tasks of atomization, excitation, and ionization.

The reasons for a lack of greater interest in the MIP among analytical laboratories are the difficulties which the MIP experiences in handling complex matrices and the difficulty the operator experiences in maintaining the plasma. The matrix problem is exemplified by a change in the magnitude and/or stability of analyte response in comparison to the response for an elemental standard during the time period in which the analytical measurement is made Satzger, Fricke, Caruso, 1988. Maintaining the plasma includes initiation, tuning, and sustaining a stable plasma which does not intersect the walls of the plasma containment tube (typically quartz) resulting in tube degradation. A stable plasma exhibits an efficient transfer of power from the microwave generator to the resonant cavity and is dependent on an impedance match between the generator and, in this case, a $TM_{010}$ resonant cavity. A poor impedance match results in current reflected back toward the microwave power supply causing heating of connectors, cables, and tuning components as well as reduced magnetron lifetime.

The microwave induced plasma used as anion source for mass spectrometry offers several potential advantages over the rf Ar ICP. The microwave cavity can readily sustain analytical plasmas in alternative gases (He, $N_2$). The use of support gases other than Ar results in simplified background spectra, which should enable the determination of $Ca^+$, $Fe^+$, and $Se^+$ using their major isotopes. Argon atomic and molecular ions listed in Table 1 overlap with these analyte ions. A helium plasma should permit determination of the Halogens (F, Cl, Br, I) and non-metals (P, B, Se, Te, As) as positive ions as a result of the higher ionization potential of He Satzger, et al., 1987. In addition to a lower capital investment, reduced gas and power consumption with the MIP result in lower operating costs. Reduced demands for heat dissipation with the smaller MIP (when compared with the ICP) decrease the rate of sampling orifice deterioration.

Recent work in these laboratories has been directed toward improving the MIP as an ion source for mass spectrometry. Two major problems were encountered when using the MIP as an ion source. The first problem was that in the tangential flow torches investigated, the tangential flow was generated by forcing gas between the inside wall of a quartz tube which contains the plasma and the outer diameter of a threaded insert. Since the threaded insert which was usually machined did not perfectly match the asymmetric quartz containment tube, an asymmetric plasma was frequently generated. As the quartz tube aged, its surface became etched and eventually required replacement. Due to the irregularity of the quartz tubing, no two containment tubes would produce the same flows or the same plasma symmetry. This resulted in a change of experimental parameters with each containment tube.

The second problem was that the two dimensional spatial distribution of analyte in a MIP sustained in a cylindrical $TM_{010}$ resonant cavity illustrated two optima. Investigators have found that analyte introduced into the plasma rapidly diffuses toward the periphery of the plasma and does not penetrate the region of greatest electron density Matousek, et al., 1989. Therefore, analyte ions extracted from the MIP by the vacuum system must be sampled from the periphery of the plasma where atmospheric gases are entrained Satzger, et al., 1988. This results in high levels of analyte oxides, hydroxides, nitrides, and other molecular ions in the background spectra which greatly increase the number of spectral interferences.

Major limitations to the use of microwave plasma as an ion reservoir for mass spectrometric detection have been the difficulties in controlling the plasma shape or location of the plasma in the discharge tube, and sample introduction into the microwave plasma. Although the MIP offers tremendous potential, most investigators agree that successful use of the MIP requires a great deal of dedication and patience.

The microwave plasma is a versatile source. A modified Beenakker-type $TM_{010}$ resonant cavity allows plasmas to be sustained in a number of gases including Ar, He, N2 and air. However, problems with instability of the plasma discharge have led to numerous torch designs. Several investigators have developed or improved tangential flow devices which control the position of the plasma in the discharge tube by high velocity gas flows and thereby reduced degradation of the torch. See, example, Haas, D.L.; Caruso, J.A. *Anal. Chem.* 1984, 56, 2014; Bollo-Kamara, A.; Codding, E.G. *Spectrochim*, Acta 1981, 36B, 973; and Michiewicz, K.G.; Urh, J.J.; Carnahan, J.W. *Spectrochim*, Acta 1985. One problem with these devices was a tangential flow which was generated by gas flowing between the inside walls of a plasma containment tube and the outer diameter of a threaded insert. The symmetry of the gas flow generated by gas flowing through these threads was dependent on the fit of the threaded insert in the containment tube. Since quartz tubing is rarely perfectly round, there will be asymmetry in the flows produced and therefore in the plasma generated. Also, the tolerances of quartz tubing are not sufficiently narrow to permit replacement of the quartz containment tube while maintaining analytical performance. This lack of a good match between insert and containment tube results in the use of elevated tangential gas flow rates, which in the case of a He plasma, can greatly increase the cost of the technique.

Additional experimental difficulties in using the MIP technique arise when the spatial distribution properties of analyte in the plasma are considered. Investigators have found that analyte introduced into the plasma rapidly diffuses toward the periphery of an inhomogeneous microwave field and does not penetrate the center of the plasma (Matousek, J.P.; Orr, B.J.; Selby M. *Appl. Spectrosc.* 1984, 38, 231; and Selby, J.; Rezaalyaan, R.; Hieftje, G.M. *Appl. Spectrosc.* 1987, 41, 7497). Therefore, when the MIP technique is used as an ion source for atomic mass spectrometry, the optimum (greatest net count rate) ion sampling position corresponds to a region in which atmospheric gases are entrained in the plasma (Satzger, R.D.; Fricke, F.L.; Caruso, J.A. *J. Anal. Atom. Spectrem.* 1988, 3, 319). As a result, high levels of analyte oxides, hydroxides, nitrides and other molecular ions are produced which increase the complexity of the background spectra.

SUMMARY OF THE INVENTION

In view of the above, it is an object of the present invention, among others, to provide a microwave induced plasma torch with improved power transfer from the microwave generator to the resonance cavity to increase the lifetime of the power generation and power transfer components.

It is another object of the present invention to provide a microwave induced plasma torch that desirably confines the analyte introduction to the center of the plasma discharge.

It is still another object of the present invention to provide a microwave induced plasma torch having improved stability.

The present invention provide a torch that operates on a He plasma gas flow rate of approximately 4 Lmin$^{-1}$ depending on power applied to the resonant cavity. This torch eliminates the necessity of a slip fit between the containment tube and the threaded insert by accomplishing this in the torch body. By using a machined press fit, symmetry of the tangential gas flow and resultant plasma is improved. A tantalum injector tube aids in coupling the resonant cavity to the generator. The injector delivers the sample through the cavity along the axis of a toroidal plasma. An atmospheric pressure sampling mass spectrometer is used to monitor analyte ionization and distribution in the plasma.

The present invention advantageously provides a microwave induced plasma torch in which plasma formation is symmetrical and in which analyte diffusion at the periphery of the plasma is eliminated by the introduction of the analyte to the resonant cavity beyond the central maximum of the electric field which provides an improvement in sensitivity of two to three orders of magnitude. The improved power transfer to the microwave cavity enables operation at lower power levels with increased operating life for the power generation and power transfer components.

Other objects and further scope of applicability of the present invention will become apparent from the detailed description to follow, taken in conjunction with the accompanying drawings, in which like parts are designated by like reference characters.

DESCRIPTION OF THE PREFERRED EMBODIMENT

Figure 1:
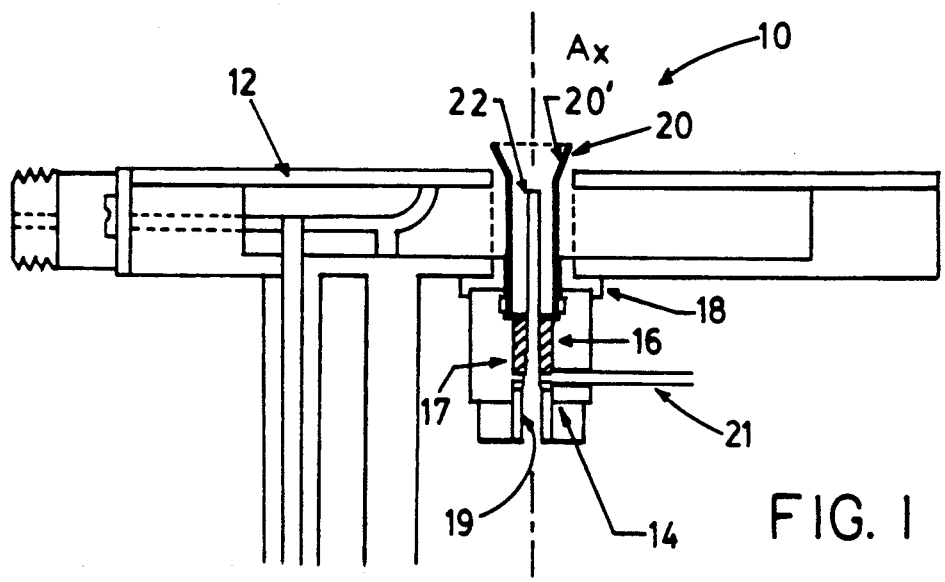
FIG. 1 is a cross-sectional view of a microwave induced plasma torch in accordance with the present invention installed in a microwave generator cavity.
Figure 2:
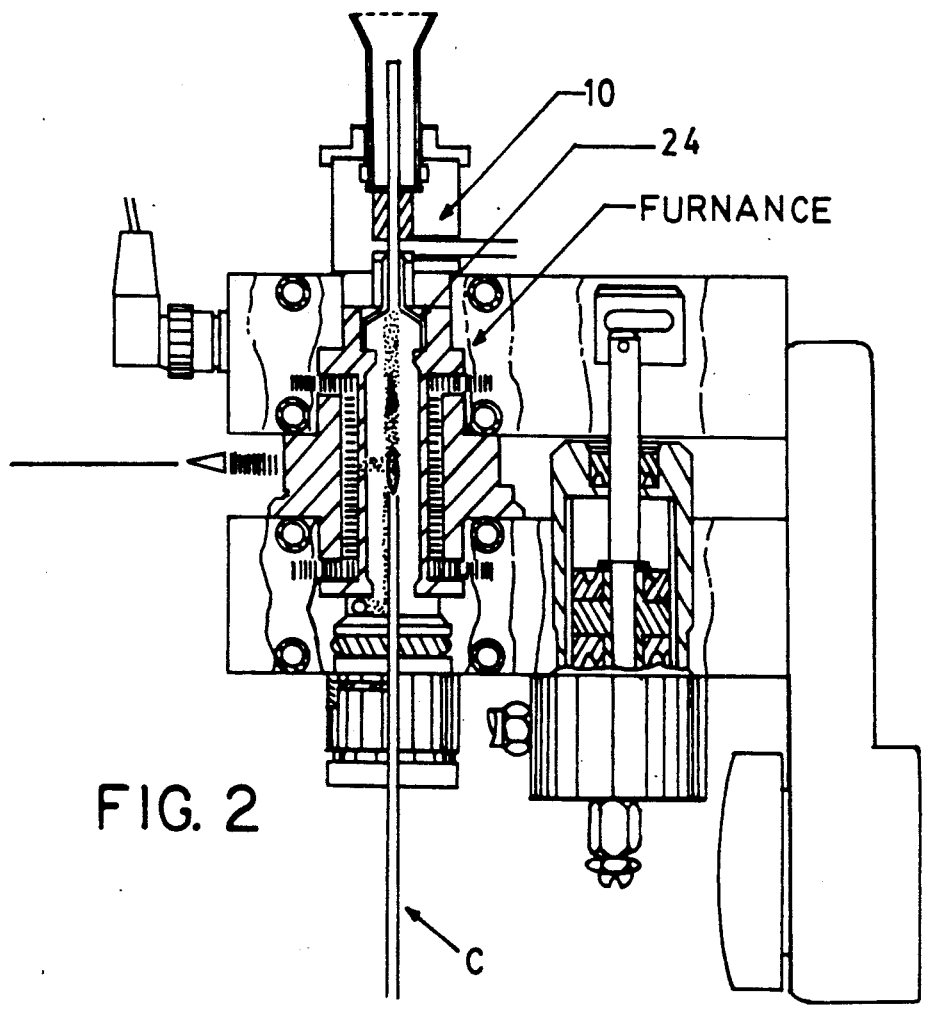
FIG. 2 is an electrothermal vaporization assembly, including a torch assembly, a quartz dome, an aluminum oxide probe tube with tungsten wire loop, and a modified PE-500 furnace assembly.

A microwave induced plasma torch in accordance with the present invention is shown in FIG. 1 and designated generally therein by the reference character 10. As shown, the torch 10 is mounted in a microwave cavity 12 that generates and transfers energy to the torch 10. The torch 10 is formed about a central longitudinal axis Ax and includes a body 14, preferably fabricated from stainless steel, a threaded insert 16, preferably fabricated from aluminum, a discoidal insulator 18 that separates and insulates the body 14 from the adjacent surfaces of the microwave cavity 12 and which is preferably fabricated from PTFE, and a quartz containment tube 20. A tantalum injector 22 is aligned generally along the longitudinal axis Ax within the containment tube 20 and through which the analyte is introduced. In order to accommodate the electrothermal vaporization (ETV) mode of sample introduction, one end of the stainless torch body 14, as shown in FIG. 2, is pressed into the downstream side of a furnace electrode block (unnumbered). Transition from the inner diameter of the electrothermally heated graphite tube vaporizer to the inner diameter of the threaded aluminum torch insert 16 is accomplished with a quartz dome 24.

In the preferred embodiment, the stainless steel torch body is 0.75" in diameter with an internal bore (unnumbered) diameter of 0.22". A length of ⅛" outer diameter stainless steel tubing 21 permits introduction of the tangential flow plasma support gas. The threaded aluminum insert 16 has 8 V-shaped (30°) simultaneous threads (represented in FIG. 1 at 17) equally spaced on a 0.22" outer diameter. There are three threads per inch at a depth of 0.008". The insert 16 is pressed into the stainless steel body 14. A 0.075" width notch 19, 0.025" deep in the aluminum insert 16 serves as a manifold to supply gas to each of the eight threads. The one-eighth inch internal diameter at the upstream end of the insert 6 accepts the quartz dome and the 1/16" internal diameter at the downstream end of the insert 16 accepts the tantalum tube injector 22. The 1/16" outer diameter tantalum injector has an 0.011" wall thickness and extends from the insert 16 through the cavity to the inside of the cavity faceplate. A one-inch length of 6 mm internal diameter by 8 mm outer diameter quartz tubing is inserted in an O-ring seal in the stainless steel body 14. The downstream end of the quartz containment tube 20 is flared outwardly (20') as shown in FIG. 1 to match the angle of the sampler. The flaired end 20' of the containment tube 20 eliminates the recirculation region formed at the sharp step of a conventional straight tube and helps reduce entrainment of atmospheric gases in the plasma. The Teflon (PTFE) insulator cap 18 is placed over the torch 10 to electrically isolate the torch body 14, which is in contact with the ETV electrode support block (FIG. 2), and to center the torch 10 in the microwave cavity 12 (FIG. 1). The entire torch/vaporization assembly is mounted on translators (not shown in the figures) enabling three-dimensional plasma profiling.

Samples are introduced onto a probe which passes through a Teflon block in the upstream window assembly (quartz window used in atomic absorption removed) as illustrated in FIG. 2. The entire O-ring seated assembly is removed for sample deposition onto the probe. The probe 26 illustrated in FIG. 2 is constructed of a 1.5 mm outer diameter ×0.8 mm internal diameter aluminum oxide tube with a 0.127 mm tungsten wire loop onto which 5 µL samples are delivered. A 1 µl drop of metallic Hg was placed into a sample reservoir (ca 20 µL volume) which was machined in the end of the graphite probe. Mercury vaporization at ambient temperature generated a steady state response.

The microwave generator 12, preferably 2450 MHz microwave generator (Micro-Now, 420-2), operates at powers up to 500 W. The microwave plasma was generated in a water cooled, 1 cm deep loop coupled $TM_{010}$ resonant cavity which incorporates a double-stub tuner and a tantalum injector probe for internal impedance matching.

The mass spectrometer is of the type described in Satzger, R.D. *Anal. Chem.* 1988, 60, 2500, the disclosure of which is incorporated herein by reference. The diameter of the sampler cone orifice was reduced to 0.4 mm. Single element pulse counting data acquisition was accomplished through a BASIC language program which was written to acquire, manipulate, and store the frequency of signal pulses which were arriving at a pulse counting ratemeter. While the pulse rate can be read directly from the ratemeter for steady-state signals, the rapid transient signals originating from ETV or direct-probe-insertion volatilization required the use of computer acquisition.

Figure 3:
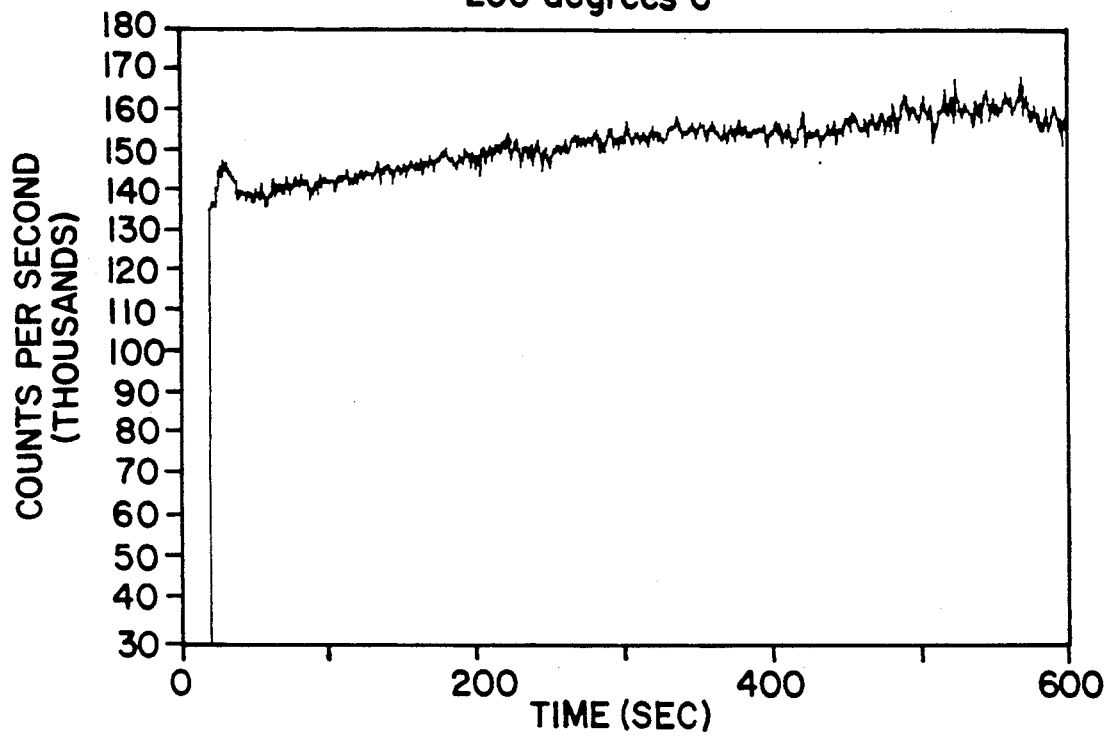
FIG. 3 is a graphical representation of the stability of response during vaporization of Hg at ambient temperature in which the vertical axis represents counts per second and the horizontal axis represents time in seconds.

Th torch 10 has demonstrated improvements in several problem areas associated with prior art torches. The stability of the plasma generated is shown in FIG. 3 during the continuous vaporization of a drop of Hg from a graphite probe in the vaporizer at ambient temperature (ca 22° C.). Plotted in FIG. 3 is the ion count rate over a period of five minutes illustrating a relative standard deviation of about 10%. Since the torch 10 is mounted in the resonant cavity, the sampling position can be reproduced after the plasma ion source has been moved out of the sampling position for containment of the injector tube replacement. The close tolerances which are maintained between the insert 16 and the torch body 14 permit the use of reduced He gas flow resulting in less turbulent flow, longer residence time, and lower operating costs. A 4 $Lmin^{-1}$ tangential He flow will sustain a 200 W plasma with no deterioration of the quartz containment tube 20 and little effect on the tantalum injector 22. The evaporation rate of the injector based on the $^{181}Ta^+$ count rate is extremely slow. After approximately 40 hours, the initial injector is still in use. Lower tangential flows may be used at lower powers. The velocity of the tangential gas flow and/or volume of gas required may be selected by using the appropriate insert groove depth and regulator pressure. With one insert used in the preferred embodiment, a regulator pressure of 50 psi enables a sufficiently wide range of flow rates (0 to 10 $Lmin^{-1}$) to investigate power levels up to 500 W without degradation of the containment tube 20, although injector tube 22 lifetime is decreased.

The low kinetic temperature of the MIP permitted the addition of the injector probe. The probe produced a toroidal plasma and enabled axial introduction of the sample beyond the most intense region of microwave radiation. With the injector in place, the plasma requires no external election "seed" for plasma initiation. When the magnetron current is increased, spontaneous initiation takes place as a result of inductive heating of the tantalum injector 22. However, with oxidation of the injector tube 22 surface, the time required for spontaneous initiation is increased. An additional benefit of the injector is improved power transfer from the microwave generator 12 to the resonant cavity. This assumption is based on a lack of heating of microwave transmission components which is associated with power reflected back toward the generator 12.

Three lengths of tantalum injector tubing were investigated. At 0.7 cm through the cavity, double maxima analyte spatial profiles were observed indicating rapid diffusion of analyte in the microwave field to the periphery of the plasma. This behavior was similar to that of analyte in the plasma without an extended injector. At 1.0 cm through the cavity, spatial profiles with a single maxima was obtained with initial estimates of 1 to 1.5 orders of magnitude improvement in response. With the injector completely through the cavity and flush with the cavity faceplate (1.3 cm), an intense electrical discharge existed between the sampler and the injector tube. The presence of this discharge made tuning of an ion optics extremely difficult. However, this problem would not exist were optical detection utilized. Samples introduced into the afterglow region of the plasma may demonstrate reduced interaction with the microwave field, i.e., fewer matrix dependent tuning problems.

Figure 4:
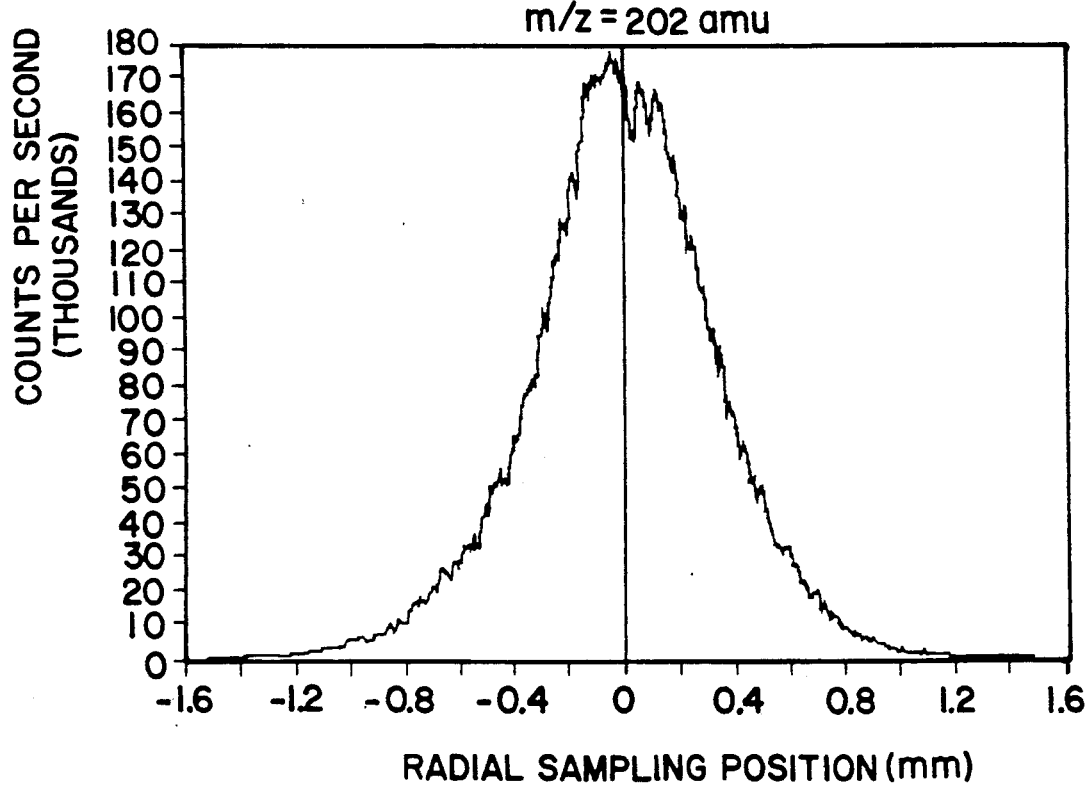
FIG. 4 is a graphical representation of the spatial profile of the $^{202}$Hg$^+$ distribution in the plasma in which the vertical axis represents counts per second (thousands) and the horizontal axis represents radial sampling position in millimeters.

Spatial profiles of analyte distribution in the plasma obtained by manually moving the plasma in 0.05 mm steps across the sampler orifice (radially) over a period of 5 minutes. Sampling depth (11 mm) and height (center) were maintained. Profiles for $^{202}Hg^+$, $^{127}T^+$, and $^{181}Ta^+$ demonstrated a maximum count rate at the center of the discharge tube. FIG. 4 illustrates the $^{202}Hg^+$ radial distribution in the plasma in which the vertical axis represents counts per second (thousands) and the horizontal axis represents radial sampling position in millimeters.

Figure 5:
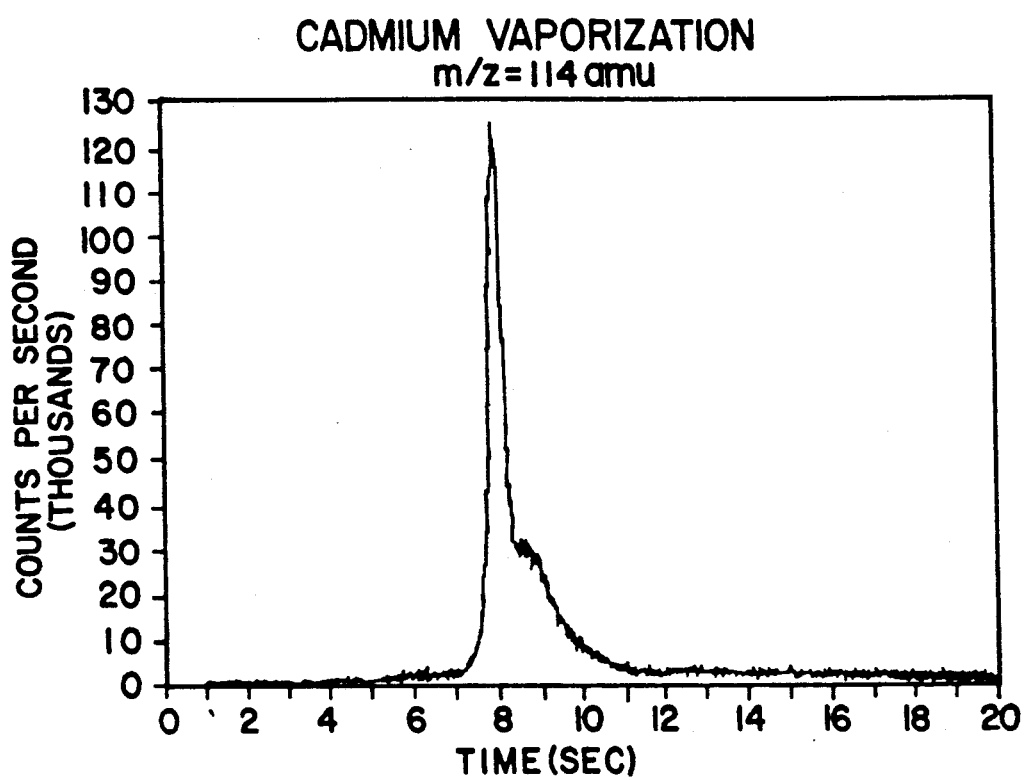
FIG. 5 is a graphical representation of the responses at m/z=114 amu during vaporization of empty furnace and 150 pg Cd in 1% HNO$_3$.
Figure 6:
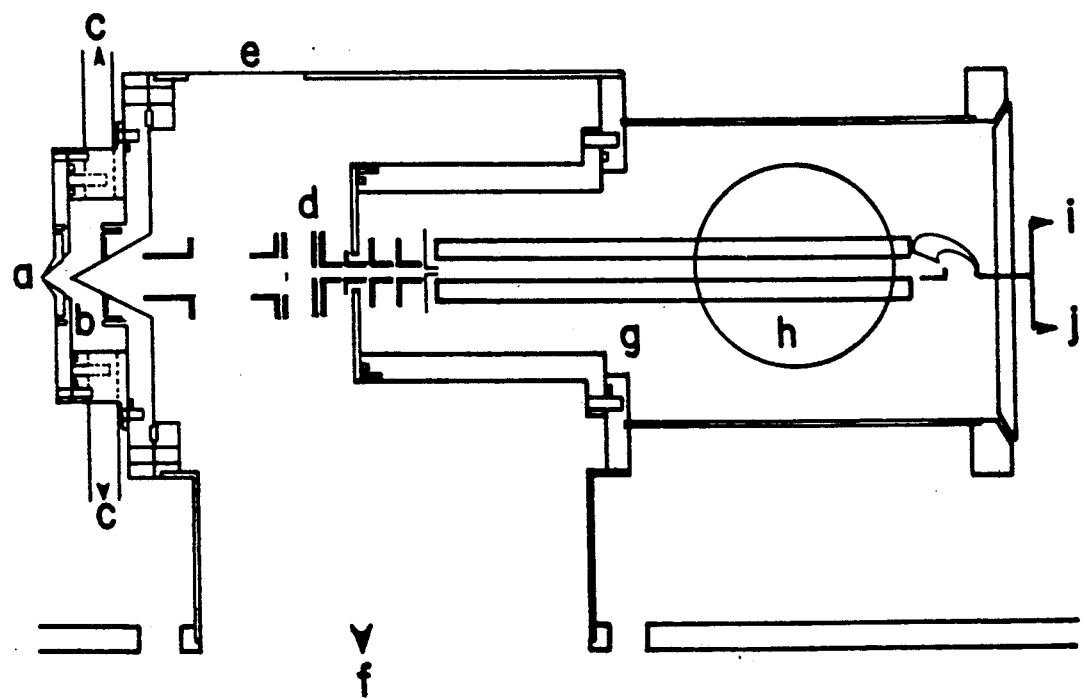
FIG. 6 is a schematic representation of an atmospheric pressure plasma sampling mass spectrometer.
Figure 7:
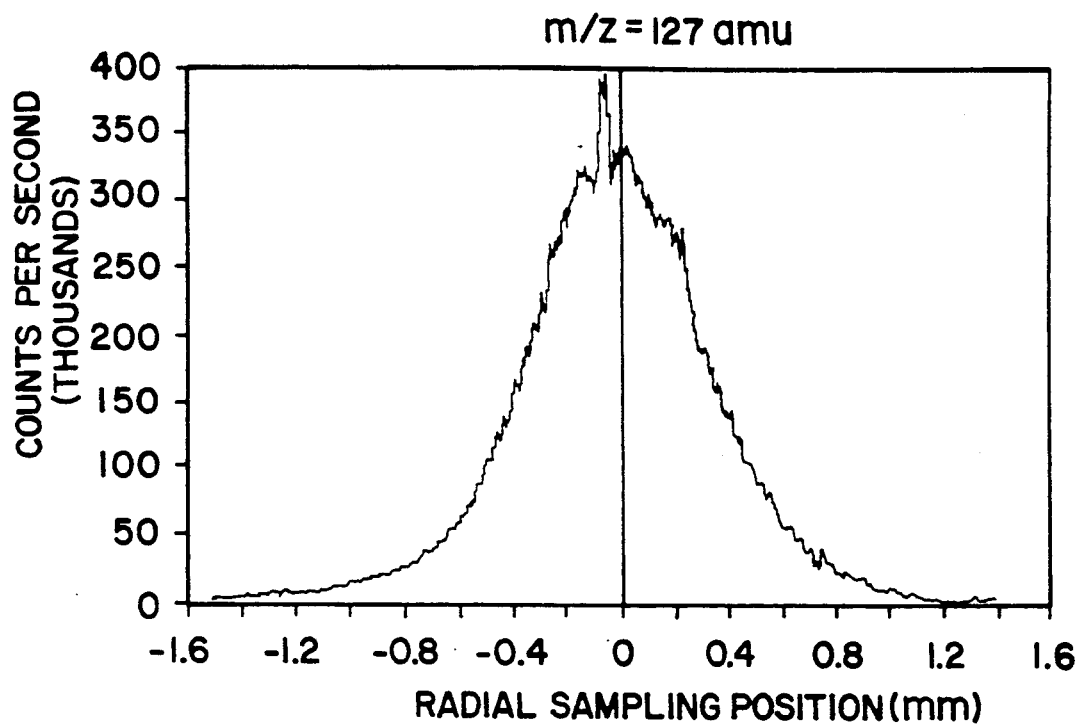
FIG. 7 is a graphical representation of the radial distribution of iodine in He plasma with a tantalum injector illustrating the central maxima in which the vertical axis represents counts per second (thousands) and the horizontal axis represents radial sampling position in millimeters.

By delivering analyte to the plasma downstream of the most intense region of the microwave field, dilution of the analyte through rapid diffusion in the field is eliminated. FIG. 5 illustrates responses for vaporization of 150 pg Cd and for a blank firing while monitoring m/z=The desirable characteristics of the microwave induced plasma (MIP) as anion source for mass spectrometry are discussed with emphasis on the analytical capabilities. Atmospheric and reduced pressure helium plasmas are described. A recently developed atmospheric pressure plasma source configuration is presented which incorporates a tantalum injector probe (MIP-TIP) and provides an improvement in sensitivity, stability, and in the efficiency of power transfer from the generator to the resonant cavity. Preliminary information obtained using both atmospheric and reduced pressure plasma sources is discussed.

The problems experienced with the MIP have been addressed in the development of a tangential flow torch which incorporates a tantalum injector probe. It is constructed of stainless steel with a threaded aluminum insert, a tantalum tube injector probe which passes completely through the 1 cm deep resonant cavity, and a quartz containment tube. Eight simultaneous threads (grooves) on the outer diameter of the Al insert conduct the tangential He flow of approximately 4 L min$^{-1}$. The forward power is approximately 60 W with less than 1 W reflected power. The sampling distance defined as the distance between the face of the resonant cavity and the tip of the sampling cone is 4 mm on center. The He sample flow is approximately 0.5 L min$^{-1}$.

The new source has improved coupling between the generator and the cavity, thereby enabling analyte ionization at reduced power. There is no heating of transmission and tuning components. The moderate power (500 W) generator has been replaced by a low power (KIVA, 100 W) generator which has greatly improved stability. The combination of improved coupling and reduced power enables operation without cooling the resonant cavity or tuning assembly. Axial introduction of analyte beyond the center of the cavity through the tantalum injector has eliminated diffusion of analyte toward the periphery of the plasma with a resultant 2-3 order of magnitude improvement in response for a given amount of analyte. Finally, improved symmetry of the tangential gas introduction has resulted in a lower rate of He consumption. A plasma can be sustained without tangential gas introduction, however, this greatly increases the spectral background.

Although solution nebulization, hydride generation, or other conventional sample introduction techniques could be utilized, sample vapor is presently introduced by electrothermal vaporization. Electrothermal vaporization has several benefits. It enables a reduction of mass spectral background due to the presence of $H_2O$; i.e., there are fewer hybrids, oxides, and hydroxides. Matrix effects can be reduced through selective volatilization of interferents. Isobaric overlap may be avoided through sequential volatilization. ETV can also be applied to volume limited, viscous, and solid samples.

Figure 8:
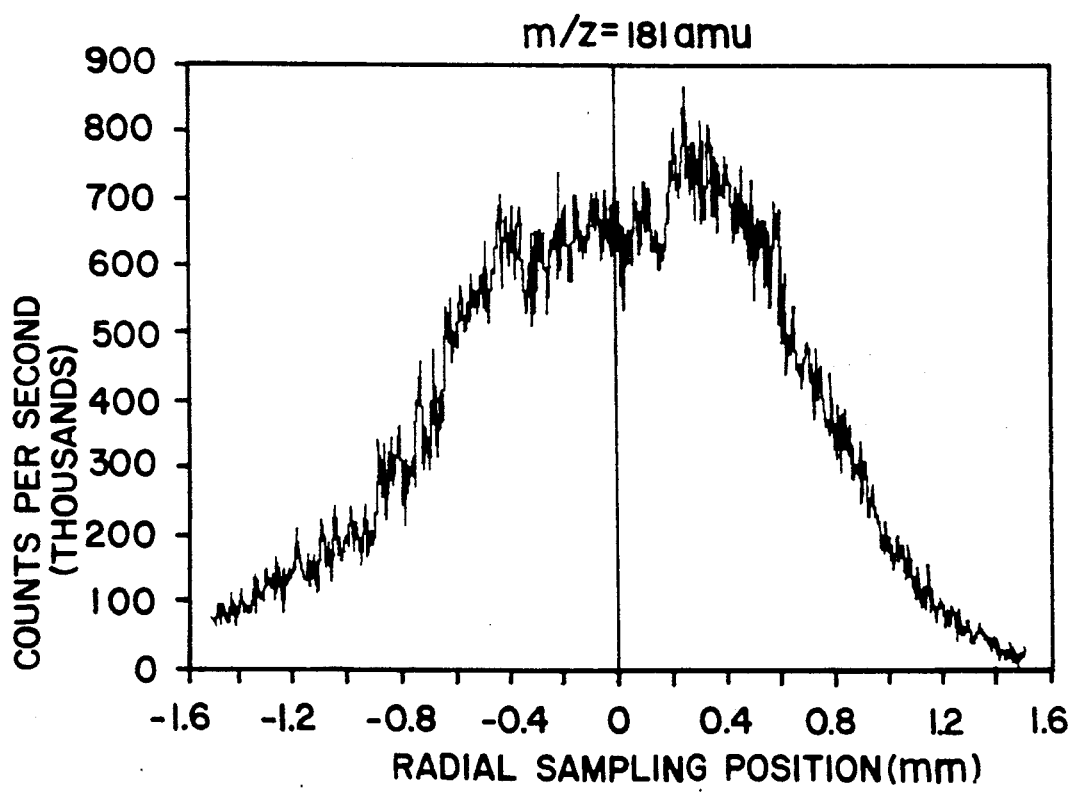
FIG. 8 is a graphical representation of the radial distribution of tantalum vaporized from the tantalum injector tube and illustrates the low vaporization rate in which the vertical axis represents counts per second and the horizontal axis represents radial sampling position in millimeters.

The distribution of analyte in the plasma was monitored by manually profiling the plasma in 0.05 mm steps across the sampler orifice. Sixty steps (3 mm total distance) were made over a period of 5 minutes. Profiles obtained for $^{202}Hg^+$, $^{127}I^+$ and $^{181}Ta^+$ are illustrated in FIGS. 3 and 4. FIG. 8 illustrates that the rate of Ta tube evaporation is not rapid. The present injector has been in operation for over 100 hours.

Figure 9:
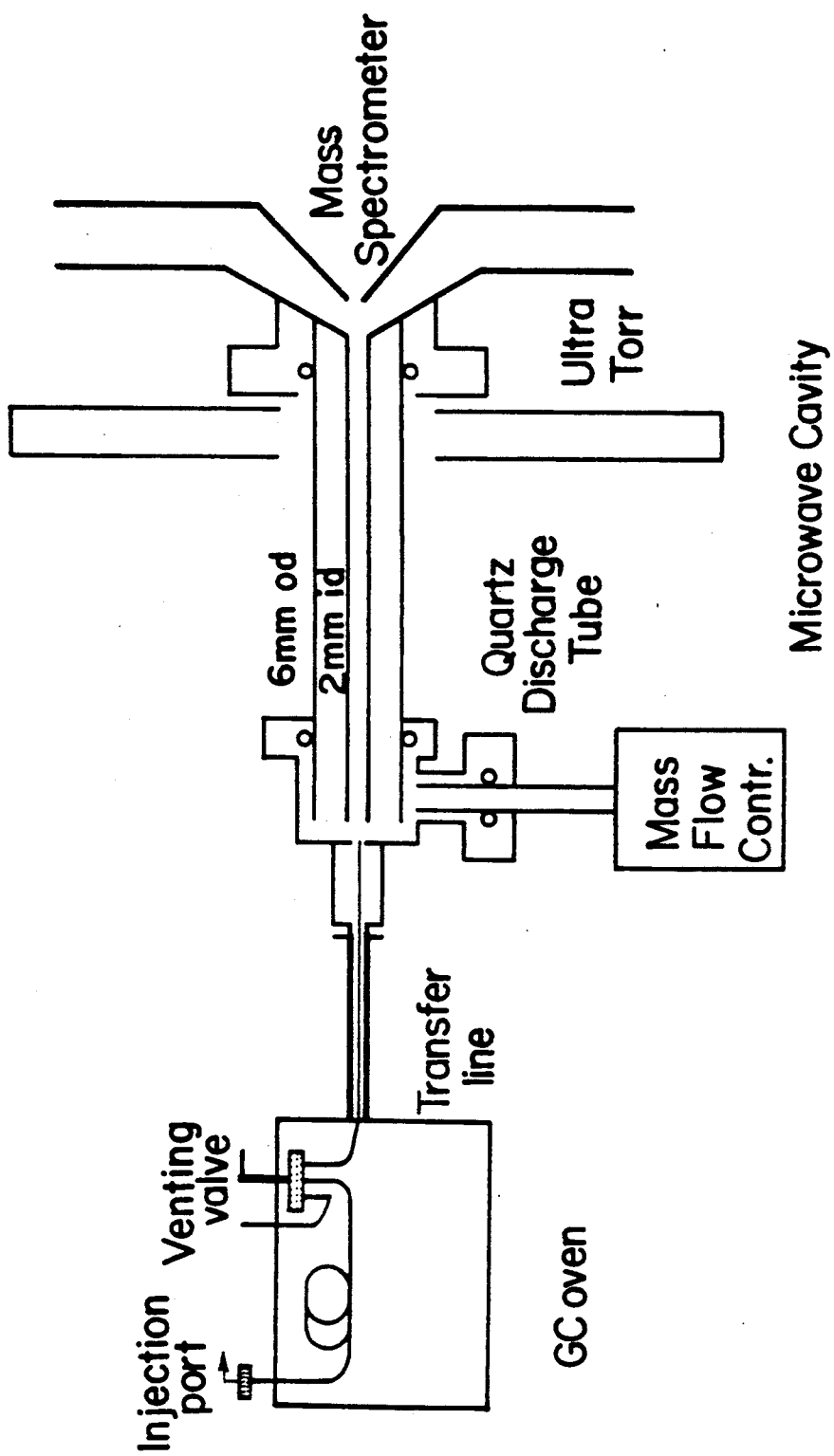
FIG. 9 is a schematic representation of a reduce pressure microwave plasma interfaced with a gas chromatograph and mass spectrometer.
Figure 10:
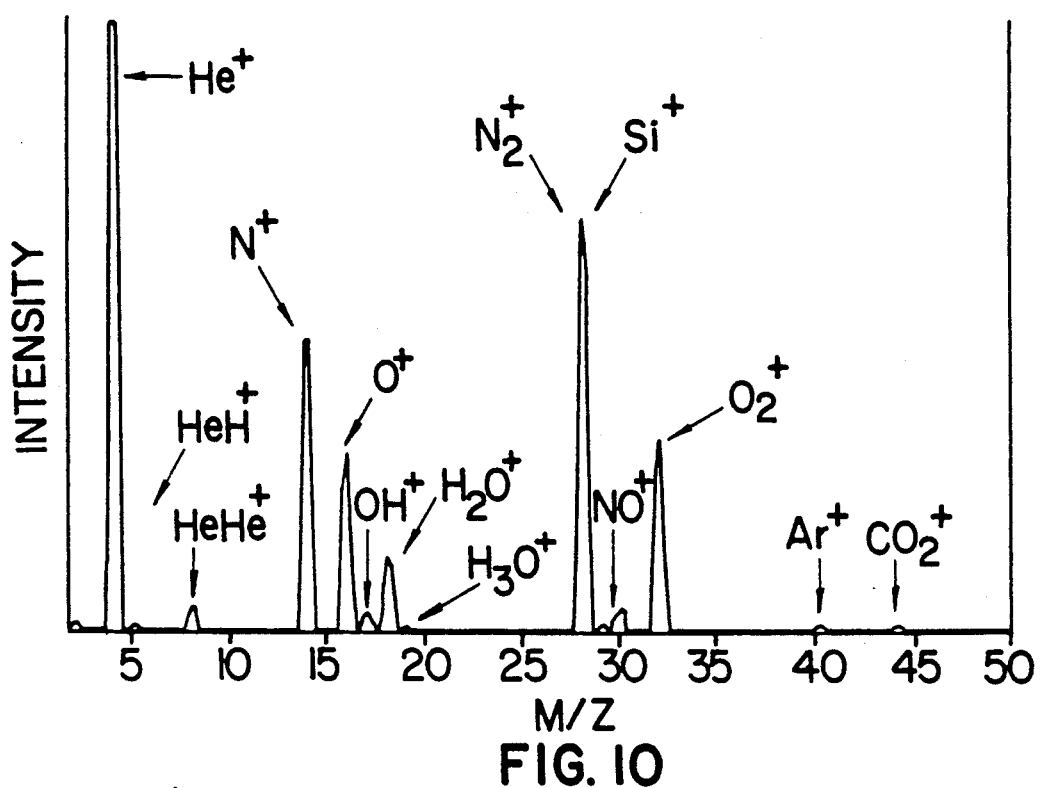
FIG. 10 is a graphical representation of the detection of iodine using reduce pressure plasma interfaced to a gas chromatograph in which the vertical axis represents intensity and the horizontal axis represents time in seconds.
Figure 11:
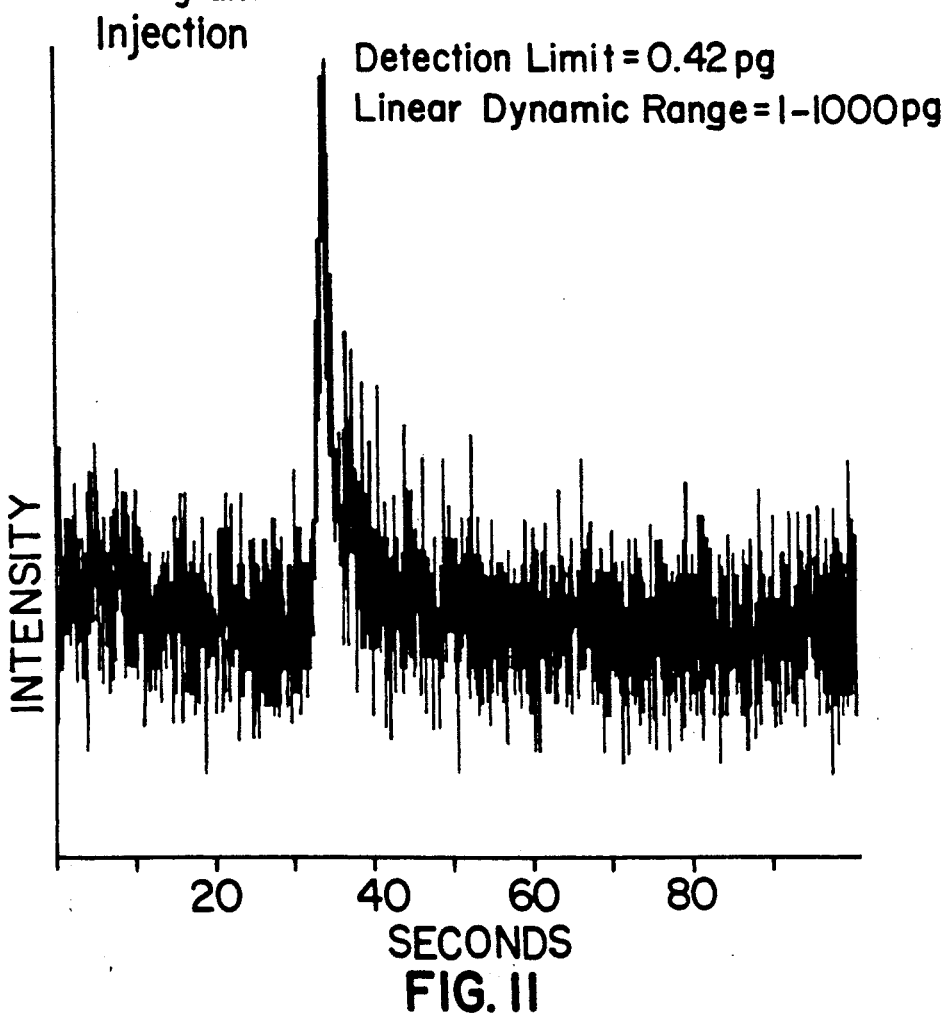
FIG. 11 represents the mass spectral background obtained with the reduced pressure He in which the vertical axis represents intensity and the horizontal axis represents M/Z.

A reduced pressure helium MIP torch has also been investigated in an effort to eliminate the molecular background species generated by atmospheric gases entrained in the atmospheric pressure plasma Creed, et al., 1988. A reduced pressure torch should represent a best case situation whereby impurities in the gas cylinder are the sole source of contaminants in the plasma. Elimination of these low mass impurities should enable ultra trade determination of $^{19}F$, $^{31}P$, $^{32}A$, $^{35}Cl$, and $^{37}Cl$. The reduced pressure MIP torch interfaced with the mass spectrometer is shown in FIG. 9. The interface involves a modification of the conventional sampler cone by addition of a vacuum tight fitting which provides a seal between the quartz discharge tube and the mass spectrometer. The sampling distance is approximately 7 mm and is defined by the distance between the sampling orifice and the face of the microwave cavity. This plasma interfaced to capillary gas chromatographic (GC) column is also illustrated in FIG. 9. A heated transfer line facilitates the transfer of analyte from the GC oven to the torch body. Preliminary results are shown in FIG. 10 which illustrates signal versus time while monitoring iodine (mz=127) which is monoisotopic. The response represents a 1 picogram injection of iodobenzene. The detection limit defined as three times the standard deviation of the background noise is 0.42 picograms. A linear response was obtained from 1 pg up to 1 ng injections. The mass spectral background obtained using the reduced pressure torch interface is shown in FIG. 11.

Although early microwave source mass spectrometric work was plagued by poor stability, high oxide levels, and diffusional dilution, the development of a tangential flow torch assembly with a Ta tube injector has led to several improvements. The transfer of power from the generator to the microwave cavity is improved, resulting in reduced heating of microwave components and the ability to operate at low power. The plasma is more symmetrical and has resulted in lower helium flow rates. The Ta injector has improved response 2-3 orders of magnitude by reduction in the dilution of analyte in the plasma gases. Temporal resolution of solvent, matrix, and analyte can be achieved, reducing their effects on analyte in the plasma. Work is continuing to evaluate the analytical capabilities of the MIP-TIP using electrothermal as well as other (GC, LC, solution nebulization, hydride) methods of sample introduction.

The reduced pressure plasma effectively eliminates the atmosphere as a source of impurities and permits determination of additional elements at ultra trace levels if high purity helium is used. A chromatographic interface has exhibited the potential for ultra trace detection of halogenated compounds. Future work will continue to evaluate the analytical capabilities of the atmospheric pressure and reduced pressure ion sources for elemental mass spectrometric determinations in nutritional and toxicological applications.

TABLE 1

| Atomic and molecular argon interferences | | |
|---|---|---|
| m/z | Element | Molecular Ion |
| *39 | K | $38_{ArH}$, $40_{Ar}$ |
| *40 | Ca | $40_{Ar}$ |
| *41 | K | $40_{ArH}$ |
| 51 | V | $36_{Ar}15_N$, $36_{Ar}14_{NH}$ |
| 52 | Cr | $40_{Ar}12_C$ |
| *54 | Fe, Cr | $40_{Ar}14_N$ |
| 55 | Mn | $40_{Ar}14_{NH}$, $(ArN,ArO)$ |
| *56 | Fe | $40_{Ar}16_O$ |
| 58 | Ni | $40_{Ar}18_O$ |
| 59 | Co | $40_{Ar}$, $18_{OH}$ |
| 74 | Ge | $36_{Ar}38_{Ar}$ |
| 75 | As | $36_{Ar}38_{ArH}$,$(40_{Ar}35_{Cl})$ |
| *80 | Se | $40_{Ar2}$ |

*Most significant argon background interferences.

The present invention advantageously provides a microwave induced plasma torch with a tantalum injector probe in which plasma formation is symmetrical and in which analyte diffusion at the periphery of the plasma is eliminated by the introduction of the analyte to the resonant cavity beyond the central maximum of the electric field which provides an improvement in sensitivity of two to three orders of magnitude. The improved power transfer to the microwave cavity enables operation at lower power levels with increased operating life for the power generation and power transfer components.

As will be apparent to those skilled in the art, various changes and modifications may be made to the illustrated microwave induced plasma torch with tantalum injector probe of the present invention without departing from the spirit and scope of the invention as determined in the appended claims and their legal equivalent.

What is claimed is:

1. A microwave induced plasma torch, comprising:
   a body member formed about a longitudinal axis and having a bore formed therein;
   a containment tube received within and extending from the bore of said body member;
   means for introducing plasma gas into said containment tube to establish a tangential gas flow in the interior of said containment tube, said gas introducing means including an insert received within the bore and having a plurality of adjacent threads opening into said containment tube;
   means for supplying plasma gas to the adjacent threads of said insert for introducing the plasma gas into said containment tube; and
   a metallic injector tube extending along the longitudinal axis and terminating at a selected position within the containment tube downstream of a resonant cavity coupling microwave energy to the introduced plasma gas, said injector tube having an outside diameter less than that of the inside diameter of said containment tube and connectable to a source of analyte, said metallic injector tube shielding the analyte from the plasma and introducing the analyte at a point beyond the central maxima of the plasma region.

2. The microwave induced plasma torch of claim 1, further comprising;
   means for directing microwave energy into said containment tube to create a plasma therein, said microwave energy means including said resonant cavity for coupling the microwave energy to the introduce plasma.

3. The microwave induced plasma torch of claim 1, wherein said insert comprises:
   a cylindrical member having an undercut cut region intermediate its ends, said plurality of adjacent threads extending from said undercut region to said containment tube.

4. The microwave induced plasma torch of claim 1, wherein said insert comprises:
   a cylindrical member received within the bore and having an first cylindrical portion in gas-tight relation with the bore, an undercut cut region intermediate its ends, and a second cylindrical portion extending toward said containment tube, said plurality of adjacent threads formed on said second cylindrical portion of said insert between said undercut region and said containment tube.

5. The microwave induced plasma torch of claim 3, further comprising:
   a plasma gas inlet opening formed in said torch body and opening into the undercut region to distribute plasma gas to said threads.

6. The microwave induced plasma torch of claim 4, further comprising:
   a plasma gas inlet opening formed in said torch body and opening into the undercut region to distribute plasma gas to said threads.

7. The microwave induced plasma torch of claim 4, wherein the threads are equally spaced about said second cylindrical end.

8. The microwave induced plasma torch of claim 7, wherein said threads are V-shaped and are formed at an angle of 30 degrees relative the longitudinal axis.

9. The microwave induced plasma torch of claim 8, wherein said plurality of threads comprise eight threads extending between said undercut region to said containment tube.

10. The microwave induced plasma torch of claim 1, wherein the distal end of said containment tube is flared outwardly.

11. The microwave induced plasma torch of claim 1, wherein said containment tube is fabricated from quartz.

12. The microwave induced plasma torch of claim 1, wherein said injector tube is fabricated from tantalum.

* * * * *